(12) United States Patent
Lin et al.

(10) Patent No.: US 10,598,619 B2
(45) Date of Patent: Mar. 24, 2020

(54) THERMAL PROPERTIES MEASURING DEVICE

(71) Applicant: Chung Yuan Christian University, Taoyuan (TW)

(72) Inventors: Po-Ting Lin, Taipei (TW); Shu-Ping Lin, Keelung (TW); Wei-Hao Lu, New Taipei (TW); Yu-Hsien Tu, Taoyuan (TW)

(73) Assignee: Chung Yuan Christian University, Taoyuan (TW)

( * ) Notice: Subject to any disclaimer, the term of this patent is extended or adjusted under 35 U.S.C. 154(b) by 240 days.

(21) Appl. No.: 15/829,994

(22) Filed: Dec. 4, 2017

(65) Prior Publication Data

US 2018/0372659 A1    Dec. 27, 2018

(30) Foreign Application Priority Data

Jun. 23, 2017    (TW) .............................. 106121028 A

(51) Int. Cl.
*G01N 25/20* (2006.01)
*G01K 7/00* (2006.01)
(Continued)

(52) U.S. Cl.
CPC .................... *G01N 25/20* (2013.01)

(58) Field of Classification Search
USPC ................... 374/43, 121, 208, 166
See application file for complete search history.

(56) References Cited

U.S. PATENT DOCUMENTS

| 5,997,174 A | 12/1999 | Wyland |
| 2009/0200279 A1* | 8/2009 | Li .................... B23K 26/0648 219/121.66 |

(Continued)

FOREIGN PATENT DOCUMENTS

| CN | 103843456 | 6/2014 |
| CN | 104634458 | 5/2015 |

(Continued)

OTHER PUBLICATIONS

"Office Action of Japan Counterpart Application," dated Apr. 16, 2019, p. 1-p. 2.

(Continued)

*Primary Examiner* — Mirellys Jagan
(74) *Attorney, Agent, or Firm* — JCIPRNET

(57) ABSTRACT

A thermal properties measuring device is for measuring a thermal property of an object to be measured. The thermal properties measuring device includes a heating element, a measurement window, and at least one thermometer. The heating element is configured to be heated to a first temperature. The measurement window and the heating element are disposed according to a specific geometric relationship. The measurement window is configured to provide a heat transfer path between the object and the heating element. The thermometer is configured to measure an initial temperature of the to-be-measured object, and to measure a measured temperature after the heating element is heated. The measured temperature of the object is different from the initial temperature of the object. The thermal property of the object is associated with the specific geometric relationship, the first temperature, the initial temperature, the measured temperature and an environment temperature.

10 Claims, 2 Drawing Sheets

(51) Int. Cl.
*G01K 1/00* (2006.01)
*G01J 5/00* (2006.01)

(56) References Cited

U.S. PATENT DOCUMENTS

2010/0292951 A1  11/2010  Gaertner et al.
2011/0062329 A1   3/2011  Ben-Bassat

FOREIGN PATENT DOCUMENTS

| JP | S60140131 | 7/1985 |
| TW | M350016 | 2/2009 |
| TW | 201024689 | 7/2010 |
| TW | I485396 | 5/2015 |
| TW | I486565 | 6/2015 |
| TW | 201721144 | 6/2017 |

OTHER PUBLICATIONS

"Office Action of Taiwan Counterpart Application," dated Mar. 2, 2018, p. 1-p. 3.

* cited by examiner

THERMAL PROPERTIES MEASURING DEVICE

CROSS-REFERENCE TO RELATED APPLICATION

This application claims the priority benefit of Taiwan application serial no. 106121028, filed on Jun. 23, 2017. The entirety of the above-mentioned patent application is hereby incorporated by reference herein and made a part of this specification.

BACKGROUND OF THE INVENTION

Field of the Invention

The invention relates to a measuring device, and particularly to a thermal properties measuring device for measuring thermal properties of a material.

Description of Related Art

Emissivity, also called a radiation coefficient, of an object is a measure of the ability of a surface of the object to release energy as thermal radiation. For easy representation, in physics, the emissivity of an object is defined as a ratio of energy emitted from the object at a specific temperature to energy radiated from a black body at the same specific temperature. In which, the emissivity of the black body is defined as 1, and the emissivity of other objects is between 0 and 1. In general, the deeper the color of a material or the rougher the surface of the material, the closer the emissivity of the material is to 1; the higher the reflectivity of the material, the lower the emissivity of the material.

Since an emissivity measurement method using a Leslie's cube was invented in 1804 by Scottish physicist John Leslie, modern measuring instruments have become more and more accurate. However, numerous precision instruments are often needed for assistance in the measurement. For example, a vacuum environment may be required for isolation from interference from an external heat source, or a material for simulating the black body may be required. In addition, it is hard to measure objects having low emissivity. Therefore, in measuring the emissivity of an object, there is often a high measurement cost and the location of measurement is also limited.

SUMMARY OF THE INVENTION

The invention provides a thermal properties measuring device whose accuracy of thermal properties measurement is free from influence of different thermal properties of a to-be-measured object, and which has both characteristics of low cost and good portability.

The thermal properties measuring device of the invention is for measuring a thermal property of a to-be-measured object. The thermal properties measuring device includes a heating element, a measurement window, and at least one thermometer. The heating element is configured to be heated to a first temperature. The measurement window and the heating element are disposed according to a specific geometric relationship. The measurement window is configured to provide a heat transfer path between the to-be-measured object and the heating element. The thermometer is configured to measure an initial temperature of the to-be-measured object, and to measure a measured temperature after the heating element is heated. The measured temperature of the to-be-measured object is different from the initial temperature of the to-be-measured object. The thermal property of the to-be-measured object is associated with the specific geometric relationship, the first temperature, the initial temperature, the measured temperature and an environment temperature.

Based on the above, in the thermal properties measuring device provided by the invention, heat transfer is induced between the heating element and the to-be-measured object, where the temperature and thermal properties of materials of the heating element are known. By observing the heat transfer between the heating element the to-be-measured object via the measurement window with reference to the initial temperature of the to-be-measured object and the environment temperature which can be directly measured, in combination with the geometric relationship between the heating element and the measurement window in the thermal properties measuring device, the thermal property of the to-be-measured object can be accurately calculated, and characteristics of low cost and good portability are both achieved.

To make the above features and advantages of the invention more comprehensible, embodiments accompanied with drawings are described in detail as follows.

DETAILED DESCRIPTION OF DISCLOSED EMBODIMENTS

Figure 1:
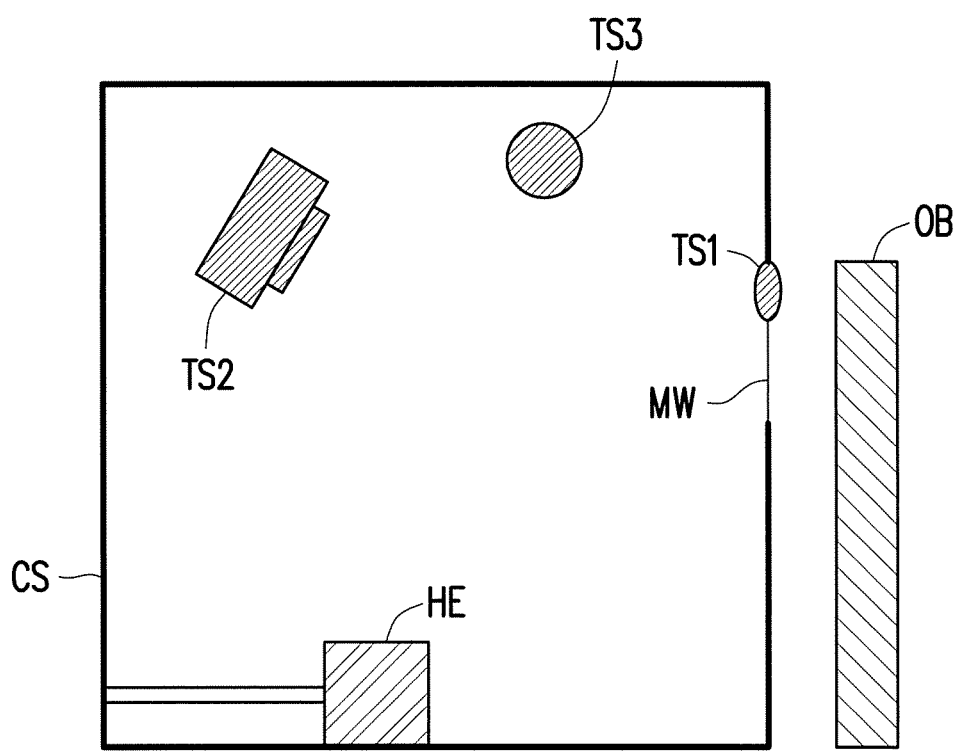
FIG. 1 illustrates a schematic diagram of installation of a thermal properties measuring device according to an embodiment of the invention.

FIG. 1 illustrates a schematic diagram of installation of a thermal properties measuring device according to an embodiment of the invention. Referring to FIG. 1, a thermal properties measuring device 100 of the present embodiment includes a heating element HE, a measurement window MW, at least one thermometer TS1 to TS3 and an encapsulating case CS. A user may, for example, cause the measurement window MW to be aligned with and to approach a to-be-measured object OB so as to measure a thermal property of the to-be-measured object OB. In the present embodiment, the measured thermal property of the to-be-measured object OB is, for example, thermal radiation emissivity of the to-be-measured object OB. Hereinafter, each element of the thermal properties measuring device 100 of the embodiment of the invention will be explained.

In the present embodiment, the heating element HE is, for example, a material having emissivity known to be $\varepsilon_H$, and can be heated to a known first temperature. However, the invention herein does not limit the actual manner of implementing the heating element HE.

For example, the heating element HE may be a material having emissivity of $\varepsilon_H$ connected to a controllable heat source. By controlling the controllable heat source, the heating element HE can be heated to the first temperature. In another embodiment, the heating element HE may be, for example, a material having emissivity of $\varepsilon_H$ connected to an uncontrollable heat source, and temperatures of the heating element HE before and after being heated are measured by installing another thermometer (not illustrated). In other words, persons of ordinary skill in the art may dispose the heating element HE according to needs to enable the heating element HE to be heated to the known first temperature. The invention is not limited thereto.

In the present embodiment, the measurement window MW is configured to provide a heat transfer path between the to-be-measured object OB and the heating element HE. Specifically, when the heating element HE is heated to the first temperature and the first temperature is higher than an initial temperature of the to-be-measured object OB, the heating element HE radiates net heat to the to-be-measured object OB via the measurement window MW. Then, after receiving the heat from the heating element HE, the to-be-measured object OB may radiate a part of the heat back into the thermal properties measuring device 100 via the measurement window MW. By observing the above heat transfer process, the thermal properties measuring device 100 of the embodiment of the invention is capable of measuring thermal properties of the to-be-measured object OB.

It is worth mentioning that, according to disposition positions and disposition angles of the heating element HE and the measurement window MW in the thermal properties measuring device 100, a specific geometric relationship is present between the heating element HE and the measurement window MW. This specific geometric relationship is directly associated with a radiation view factor between the heating element HE and the measurement window MW and a radiation view factor between the measurement window MW and each of the thermometers TS1 to TS3. In addition to the disposition positions and disposition angles of the heating element HE and the measurement window MW in the thermal properties measuring device 100, the above radiation view factors are also associated with surface area and surface shapes of the heating element HE, the measurement window MW and each of the thermometers TS1 to TS3 during transfer of heat radiation. Persons of ordinary skill in the art may obtain teachings associated with the radiation view factors from thermodynamics-related literatures. Therefore, details thereof are omitted herein.

In the present embodiment, at least one thermometer is configured to measure the initial temperature of the to-be-measured object OB before the heating element HE is heated, and to measure a measured temperature of the to-be-measured object OB after the heating element HE is heated to the first temperature. In the present embodiment, the at least one thermometer includes a first thermometer TS1, a second thermometer TS2 and a third thermometer TS3. However, the invention is not limited thereto. In other words, according to needs, persons of ordinary skill in the art may dispose a plurality of thermometers for respectively measuring temperatures (e.g., the initial temperature or measured temperature of the to-be-measured object OB, etc.).

In the present embodiment, the first thermometer TS1 is disposed at the measurement window MW and is configured to measure the initial temperature of the to-be-measured object OB before the heating element HE is heated. The second thermometer TS2 is, for example, disposed inside the encapsulating case CS, and is configured to measure the measured temperature of the to-be-measured object OB after the heating element HE is heated to the first temperature. The third thermometer TS3 is, for example, disposed inside the encapsulating case CS along with the second thermometer TS2, and is configured to measure an environment temperature inside the encapsulating case CS or an environment temperature of an environment in which the second thermometer TS2 is used.

Particularly, under an actual use scenario, as described above, the measured temperature is, for example, a temperature measured by the second thermometer TS2 when the to-be-measured object OB has received radiant heat from the heating element HE heated to the first temperature (which is, for example, higher than the initial temperature of the to-be-measured object OB) and transfers the heat back. Therefore, the measured temperature of the to-be-measured object OB is different from the initial temperature of the to-be-measured object OB, and the initial temperature of the to-be-measured object OB may be the same as or different from the environment temperature.

However, the at least one thermometer may also, for example, include more than or fewer than three thermometers. In another embodiment, the at least one thermometer may, for example, only include the second thermometer TS2 and the third thermometer TS3. The second thermometer TS2 measures the initial temperature and the measured temperature of the to-be-measured object OB respectively before the heating element HE is heated and after the heating element HE is heated to the first temperature, and the third thermometer TS3 measures the environment temperature. In still another embodiment, the at least one thermometer may further include, in addition to the first thermometer TS1, the second thermometer TS2 and the third thermometer TS3, a fourth thermometer configured to measure a temperature of the heating element HE.

Additionally, the embodiment of the invention herein does not limit the actual manner of implementing each of the thermometers. In an embodiment, each of the thermometers may be, for example, a thermal imager, converting radiant heat into an electric signal (e.g., voltage value). Electric signals of different amplitudes represent different temperatures. More specifically, the embodiment of the invention herein does not limit the form of data acquired during temperature measurement. Persons of ordinary skill in the art may select elements such as the thermometers and so on for sensing temperatures according to needs, and different elements may provide different data forms.

As installed in FIG. 1, the thermal properties measuring device 100 of the present embodiment is capable of measuring the initial temperature of the to-be-measured object OB before the net heat is transferred from the heating element HE to the to-be-measured object OB. Moreover, after the heating element HE is heated to the first temperature and the net heat is transferred to the to-be-measured object OB via the measurement window MW, the measured temperature of the to-be-measured object OB is measured. In this way, in the present embodiment, the thermal property (i.e., the thermal radiation emissivity) measured by the thermal properties measuring device 100 is expressed by the following Equation (1):

$$\varepsilon_{TBM} = F \cdot \varepsilon_H \cdot \left[ \frac{(T_H^4 - T_{IN}^4)}{(T_M^4 - T_{EN}^4)} \right]. \tag{1}$$

In the above, $\varepsilon_{TBM}$ represents the thermal radiation emissivity of the to-be-measured object OB; F represents a coefficient associated with the radiation view factor between the heating element HE and the measurement window MW and the radiation view factor between the measurement window MW and the thermometer TS2; $\varepsilon_H$ represents thermal radiation emissivity of the heating element HE; $T_H$ represents the first temperature; $T_{IN}$ represents the initial temperature of the to-be-measured object OB; $T_M$ represents the measured temperature of the to-be-measured object OB and $T_{EN}$ represents the measured environment temperature. In the present embodiment, the coefficient F is a ratio of the radiation view factor between the heating element HE and the measurement window MW to the radiation view factor between the measurement window MW and the thermometer TS2.

It is worth mentioning that, the embodiment of the invention does not limit or describe any details of acquisition of data from each element in the embodiment of FIG. 1. For example, the data (e.g., data of the temperatures) of the at least one thermometer TS1 to TS3 and the heating element HE may be transferred in a wired manner by connecting the at least one thermometer TS1 to TS3 and the heating element HE to a port of the encapsulating case CS. However, the invention is not limited thereto.

Figure 2:
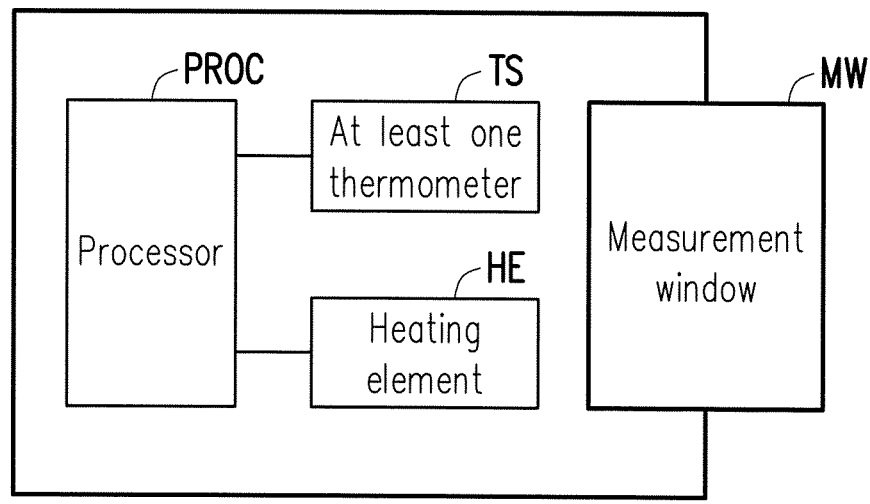
FIG. 2 illustrates a schematic block diagram of a thermal properties measuring device according to an embodiment of the invention.

FIG. 2 illustrates a schematic block diagram of a thermal properties measuring device according to an embodiment of the invention. Referring to FIG. 2, the thermal properties measuring device 100 of the embodiment of FIG. 1, for example, further includes a processor PROC, and thus becomes a thermal properties measuring device 200 of the present embodiment. In the present embodiment, the thermal properties measuring device 200 includes the heating element HE, the measurement window MW, at least one thermometer TS and the processor PROC, wherein the same reference numerals denote the same or similar elements as those in the aforementioned embodiment, and details thereof are thus omitted herein.

In the present embodiment, the heating element HE, the measurement window MW, the at least one thermometer TS and the processor PROC are, for example, disposed inside an encapsulating case, so as to form the handheld thermal properties measuring device 200. The user may, for example, hold the thermal properties measuring device 200 of the present embodiment by hand, and cause the measurement window MW to be aligned with and to approach a to-be-measured object, so as to measure a thermal property (e.g., thermal radiation emissivity) of the to-be-measured object.

In the present embodiment, the processor PROC is coupled to the heating element HE and the at least one thermometer TS. A radiation view factor between the heating element HE and the measurement window MW is set in the processor PROC. Accordingly, the processor PROC is capable of calculating the thermal radiation emissivity of the to-be-measured object by, for example, the aforementioned Equation (1).

In an embodiment, the handheld thermal properties measuring device 200 may, for example, further include a display element (not illustrated) coupled to the processor PROC and configured to display therein the thermal property of the to-be-measured object after the thermal property is calculated by the processor PROC.

Figure 3:
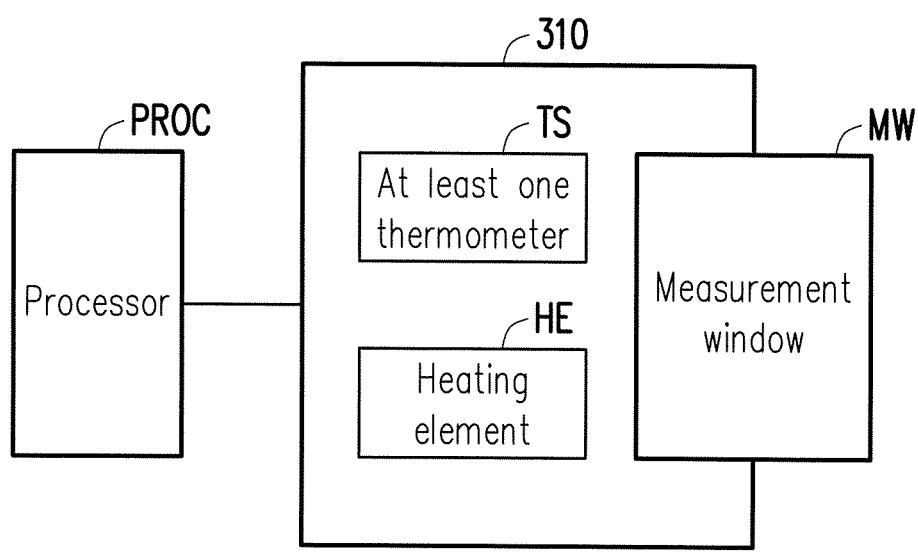
FIG. 3 illustrates a schematic block diagram of a thermal properties measuring device according to another embodiment of the invention.

FIG. 3 illustrates a schematic block diagram of a thermal properties measuring device according to an embodiment of the invention. Referring to FIG. 3, the thermal properties measuring device 100 of the embodiment of FIG. 1, for example, further includes the processor PROC, and thus becomes a thermal properties measuring device 300 of the present embodiment. In the present embodiment, the thermal properties measuring device 300 includes the heating element HE, the measurement window MW, at least one thermometer TS and the processor PROC, wherein the same reference numerals denote the same or similar elements as those in the aforementioned embodiment, and details thereof are thus omitted herein.

The present embodiment differs from the embodiment of FIG. 2 in that, in the present embodiment, the heating element HE, the measurement window MW and the at least one thermometer TS are, for example, disposed inside an encapsulating case, so as to form a handheld measuring element 310, the handheld measuring element 310 being externally connected to the processor PROC. In the present embodiment, the user may, for example, hold the handheld measuring element 310 by hand, and cause the measurement window MW to be aligned with and to approach the to-be-measured object, so as to measure an initial temperature and a measured temperature of the to-be-measured object. Then, the acquired initial temperature and measured temperature are provided to the processor PROC. According to the preset radiation view factor between the heating element HE and the measurement window MW, the preset radiation view factor between the measurement window MW and the at least one thermometer TS, the thermal radiation emissivity of the heating element HE, the first temperature of the heating element HE after heating, the environment temperature of the measurement environment, and the initial temperature and measured temperature acquired by the handheld measuring element 310, the processor PROC calculates the thermal radiation emissivity of the to-be-measured object based on the aforementioned Equation (1).

Similarly, the processor PROC of the present embodiment may be further coupled to the display element (not illustrated) so as to display a calculation result of the processor PROC in the display element.

It is worth mentioning that, the thermal properties measuring device of the embodiment of the invention observes heat radiation coming from the heating element and reflected by the to-be-measured object. Therefore, when the to-be-measured object is opaque, or made of an opaque material, the thermal properties measuring device provided by the embodiment of the invention will achieve a more accurate measurement result.

In summary, in the thermal properties measuring device provided by the embodiment of the invention, heat transfer is induced between the heating element and the to-be-measured object, wherein the temperature and thermal properties of materials of the heating element are known. By observing the heat transfer between the heating element the to-be-measured object via the measurement window with reference to the initial temperature of the to-be-measured object and the environment temperature which can be directly measured, in combination with the geometric relationship between the heating element and the measurement window in the thermal properties measuring device, the thermal property of the to-be-measured object can be accurately calculated, and characteristics of low cost and good portability are both achieved.

Although the invention has been described with reference to the above embodiments, it will be apparent to one of ordinary skill in the art that modifications to the described embodiments may be made without departing from the spirit of the invention. Accordingly, the scope of the invention will be defined by the attached claims and not by the above detailed descriptions.

What is claimed is:

1. A thermal properties measuring device configured to measure a thermal property of a to-be-measured object, the thermal properties measuring device comprising:

a heating element configured to be heated to a first temperature;

a measurement window configured to provide a heat transfer path between the to-be-measured object and the heating element, wherein the heating element and the measurement window are disposed according to a geometric relationship; and at least one thermometer configured to measure an initial temperature of the to-be-measured object, and to measure a measured temperature of the to-be-measured object after the heating element is heated to the first temperature, wherein the initial temperature is different from the measured temperature, wherein the thermal property of the to-be-measured object is associated with the geometric relationship, a thermal property of the heating element, the first temperature, the initial temperature, the measured temperature, and an environment temperature inside an encapsulating case or an environment temperature of an environment in which one of the at least one thermometer is used.

2. The measuring device according to claim 1, wherein each of the thermal property of the to-be-measured object and the thermal property of the heating element is a thermal radiation emissivity.

3. The measuring device according to claim 1, wherein the at least one thermometer comprises:

a first thermometer disposed at the measurement window and configured to measure the initial temperature of the to-be-measured object before the heating element is heated; and a second thermometer configured to measure the measured temperature of the to-be-measured object after the heating element is heated to the first temperature.

4. The measuring device according to claim 1, wherein the to-be-measured object is opaque.

5. The measuring device according to claim 1, wherein the geometric relationship is associated with a radiation view factor between the heating element and the measurement window and a radiation view factor between the measurement window and each thermometer.

6. The measuring device according to claim 5, wherein each of the thermal property of the to-be-measured object and the thermal property of the heating element is a thermal radiation emissivity, and the thermal property of the to-be-measured object is associated with the geometric relationship, the thermal property of the heating element, the first temperature, the initial temperature, the measured temperature and the environment temperature based on the following equation:

$$\varepsilon_{TBM} = F \cdot \varepsilon_H \cdot \left[ \frac{(T_H^4 - T_{IN}^4)}{(T_M^4 - T_{EN}^4)} \right],$$

wherein $\varepsilon_{TBM}$ represents the thermal property of the to-be-measured object, F represents a coefficient associated with the radiation view factor between the heating element and the measurement window and the radiation view factor between the measurement window and each thermometer, $\varepsilon_H$ represents the thermal property of the heating element, $T_H$ represents the first temperature, $T_{IN}$ represents the initial temperature, $T_M$ represents the measured temperature and $T_{EN}$ represents the environment temperature.

7. The measuring device according to claim 1, further comprising:

a processor coupled to the heating element and the at least one thermometer, configured to calculate the thermal property of the to-be-measured object according to the geometric relationship, the thermal property of the heating element, the first temperature, the initial temperature, the measured temperature and the environment temperature.

8. The measuring device according to claim 7, wherein the heating element, the measurement window, the at least one thermometer and the processor are disposed inside the encapsulating case, to form a handheld thermal properties measuring device.

9. The measuring device according to claim 7, wherein the heating element, the measurement window and the at least one thermometer are disposed inside the encapsulating case, to form a handheld measuring element, and the processor is externally connected to the handheld measuring element.

10. The measuring device according to claim 7, wherein one of the at least one thermometer is configured to measure the environment temperature.

* * * * *